(12) United States Patent
Ross

(10) Patent No.: US 8,537,004 B2
(45) Date of Patent: Sep. 17, 2013

(54) VERIFICATION OF DISPENSED ITEMS

(75) Inventor: Graham Ross, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 412 days.

(21) Appl. No.: 12/571,221

(22) Filed: Sep. 30, 2009

(65) Prior Publication Data

US 2011/0074576 A1 Mar. 31, 2011

(51) Int. Cl.
*G08B 21/00* (2006.01)

(52) U.S. Cl.
USPC ............ 340/540; 340/541; 600/300; 600/577

(58) Field of Classification Search
USPC ....... 340/540, 541, 309.16, 825.49; 600/300, 600/577
See application file for complete search history.

(56) References Cited

U.S. PATENT DOCUMENTS

| | | | |
|---|---|---|---|
| 5,597,995 A | 1/1997 | Williams et al. | |
| 6,192,070 B1 | 2/2001 | Poon et al. | |
| 6,535,637 B1 | 3/2003 | Wootton et al. | |
| 6,771,369 B2 | 8/2004 | Rzasa et al. | |
| 7,028,723 B1 | 4/2006 | Alouani et al. | |
| 7,545,257 B2 * | 6/2009 | Brue | 340/309.16 |
| 2003/0222548 A1 * | 12/2003 | Richardson et al. | 312/209 |
| 2004/0054436 A1 * | 3/2004 | Haitin et al. | 700/236 |
| 2005/0263537 A1 | 12/2005 | Gerold et al. | |
| 2006/0079994 A1 | 4/2006 | Chu et al. | |
| 2006/0098193 A1 | 5/2006 | Rzasa et al. | |
| 2006/0124656 A1 | 6/2006 | Popovich, Jr. | |
| 2007/0135790 A1 * | 6/2007 | Auerbach | 604/500 |
| 2008/0056556 A1 | 3/2008 | Eller et al. | |
| 2008/0316045 A1 * | 12/2008 | Sriharto et al. | 340/825.49 |
| 2009/0014458 A1 * | 1/2009 | Heffron | 221/2 |
| 2011/0015782 A1 * | 1/2011 | Chudy et al. | 700/237 |

FOREIGN PATENT DOCUMENTS

| | | |
|---|---|---|
| EP | 0 208 029 A1 | 1/1987 |
| JP | 9-253164 | 9/1997 |
| JP | 2005-279228 | 10/2005 |
| WO | 01/08106 A2 | 2/2001 |
| WO | 03/014871 A2 | 2/2003 |
| WO | 2009/006729 A1 | 1/2009 |
| WO | 2009/012371 A2 | 1/2009 |
| WO | 2009/023858 A2 | 2/2009 |

OTHER PUBLICATIONS

International Search Report, Aug. 4, 2011, pp. 4.

* cited by examiner

*Primary Examiner* — Tai T Nguyen
(74) *Attorney, Agent, or Firm* — McDermott Will & Emery LLP

(57) ABSTRACT

An automated medication dispensing system is disclosed. The system includes a memory configured to store identifying information for at least one item. The identifying information includes an indicator associated with at least one specific feature of the at least one item. The system also includes a processor configured to dispense the at least one item to a user, an output module configured to display the identifying information for the at least one item, and an input device configured to receive, from the user, input indicating that the user has verified that the dispensed item has the same identifying information as the identifying information displayed by the output module. Handheld devices, bedside administration systems, methods, and machine-readable mediums are also disclosed.

13 Claims, 4 Drawing Sheets

VERIFICATION OF DISPENSED ITEMS

BACKGROUND

1. Field

The present disclosure generally relates to systems and methods for inventory management, and, in particular, relates to the verification of items dispensed from an inventory.

2. Description of the Related Art

It is well known in the medical community, and in particular, in hospitals, to provide centrally located medication and supply dispensing stations, such as wall cabinets, manually secured patient cassette drawers, and automated dispensing machines. Such generally accessible dispensing stations serve several functions including the distribution of medicines and supplies to patient caregivers.

Although generally serving their intended purpose, there are disadvantages to such dispensing stations. One disadvantage is that the caregiver can receive or otherwise obtain the an incorrect medication from the dispensing station. This may be the result of the caregiver manually removing the incorrect medication from the dispensing station, or, in the case of automated dispensing machines, the automated dispensing machine dispensing the incorrect medication to the caregiver. Providing the incorrect medication to a patient can result in serious harm or death.

One attempt to address this disadvantage is for the caregiver to verify that they have received the correct medication. This is commonly achieved by the caregiver reading the text label on the medication or using a barcode scanner to scan a barcode associated with the medication. A caregiver, however, may incorrectly read the text label or not read the text label at all. Using a barcode scanner to scan the barcode takes additional time. In both instances, the text and/or barcode label of the medication may also be incorrect or missing.

SUMMARY

Embodiments of the dispensed item verification system disclosed herein assist a user in verifying an item dispensed by the system, such as by highlighting or otherwise prominently indicating to the user identifying features of the dispensed item. In certain embodiments, the system requires the user to provide input verifying the dispensed item is the same item requested from the system by the user.

In certain embodiments of the disclosure, an automated medication dispensing system is disclosed. The system includes a memory configured to store identifying information for at least one item. The identifying information includes an indicator associated with at least one specific feature of the at least one item. The system also includes a processor configured to dispense the at least one item to a user, an output module configured to display the identifying information for the at least one item, and an input device configured to receive, from the user, input indicating that the user has verified that the dispensed item has the same identifying information as the identifying information displayed by the output module.

In certain embodiments of the disclosure, a handheld device is disclosed. The device includes a memory configured to store identifying information for at least one item. The identifying information includes an indicator associated with at least one specific feature of the at least one item. The device also includes a processor configured to receive information identifying that the at least one item has been dispensed to a user, a display module configured to display the identifying information for the at least one item, and an input device configured to receive, from the user, input indicating that the user has verified that the dispensed item has the same identifying information as the identifying information displayed by the display module.

In certain embodiments of the disclosure, a bedside administration system is disclosed. The system includes a cabinet housing configured to hold at least one item and configured to be accessed by an authorized user, and a memory configured to store identifying information for the at least one item. The identifying information includes an indicator associated with at least one specific feature of the at least one item. The system also includes a processor configured to dispense, from the cabinet housing, the at least one item to the authorized user, an output module configured to display the identifying information for the at least one item, and an input device configured to receive, from the user, input indicating that the user has verified that the dispensed item has the same identifying information as the identifying information displayed by the output module.

In certain embodiments of the disclosure, a method for verifying the dispensing of an item is disclosed. The method includes receiving a selection for at least one item to be dispensed, dispensing the at least one item to a user, and retrieving identifying information for the at least one item from memory. The identifying information includes an indicator associated with at least one specific feature of the at least one item. The method also includes displaying the identifying information for the at least one item, and receiving, from the user, input indicating that the user has verified that the dispensed at least one item has the same identifying information as the displayed identifying information.

In certain embodiments of the disclosure, a computer-readable medium having computer-executable instructions for causing a processor to execute instructions to verify the dispensing of an item by performing steps is disclosed. The steps include receiving a selection for at least one item to be dispensed, dispensing the at least one item to a user, and retrieving identifying information for the at least one item from memory. The identifying information includes an indicator associated with at least one specific feature of the at least one item. The steps also include displaying the identifying information for the at least one item, and receiving, from the user, input indicating that the user has verified that the dispensed at least one item has the same identifying information as the displayed identifying information.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

There is a problem, in dispensing stations, of dispensed items being improperly verified or not verified at all. Previously implemented verification techniques are often inaccurate, ineffective, and/or time consuming. This and other problems are addressed and solved, at least in part, by embodiments of the present disclosure, which include an automated medication dispensing system. The system includes a memory configured to store identifying information for at least one item. The identifying information includes an indicator associated with at least one specific feature of the at least one item. The system also includes a processor configured to dispense the at least one item to a user, an output module configured to display the identifying information for the at least one item, and an input device configured to receive, from the user, input indicating that the user has verified that the dispensed item has the same identifying information as the identifying information displayed by the output module.

In the following detailed description, numerous specific details are set forth to provide a full understanding of the present disclosure. It will be obvious, however, to one ordinarily skilled in the art that the embodiments of the present disclosure may be practiced without some of these specific details. In other instances, well-known structures and techniques have not been shown in detail not to obscure the disclosure.

Figure 1:
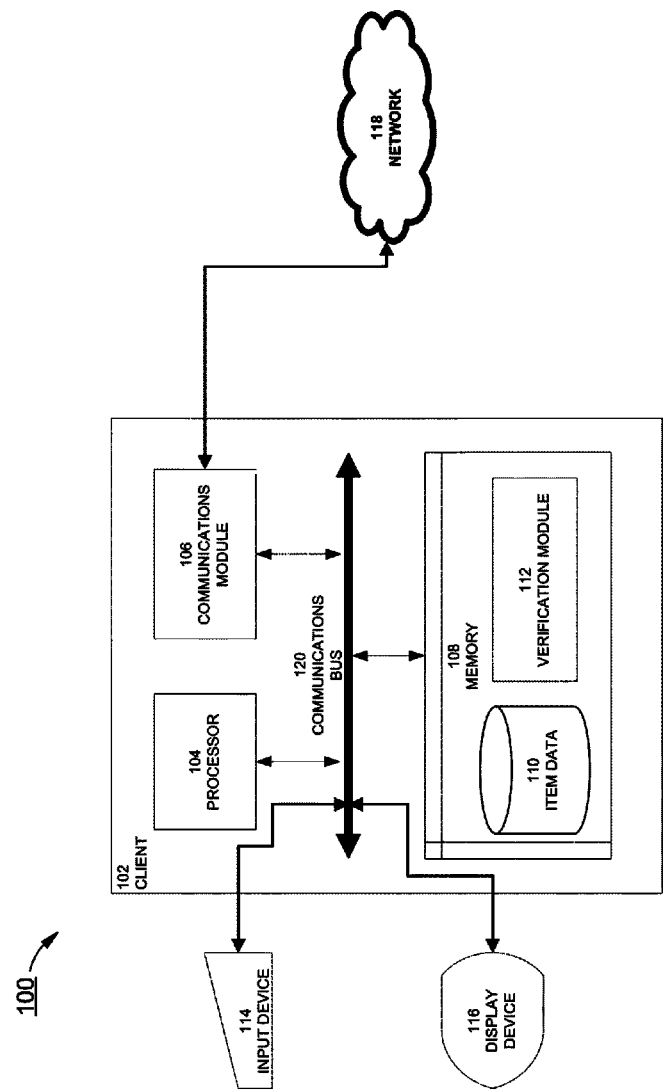
FIG. 1 is a diagram illustrating a dispensed item verification system according to certain embodiments.

FIG. 1 is a diagram illustrating a dispensed item verification system 100 according to certain embodiments. The system 100 includes a client 102, input device 114, and a display device 116. As discussed herein, the client 102 is a computer system. In certain embodiments, the client 102 is an automated dispensing machine (301 in FIG. 3A). In certain embodiments, the client 102 is a bedside administration system (351 in FIG. 3B). In certain embodiments, the client 102 is connected to a network 118. The processor 104, communications module 106, memory 108, input device 114, and display device 116 communicate using a communications bus 120.

The memory 108 of the client 102 includes an item data 110 store and a verification module 112. The item data 110 includes identifying information for items such as medications. Identifying information includes, without limitation, the following medication identifiers: images, names, doses, manufacturers, colors, sizes, shapes, tastes, weights, mass, expiration dates, manufacturing dates, markings, and barcodes. For example, an image of a medication may include a picture of a red and yellow colored pill that includes markings such as a manufacturer's name, the name of the medication, a dose of the medication, and an associated expiration date. In certain embodiments, additional identifiers that highlight or otherwise indicate specific features of the items are provided as described below with reference to FIGS. 3A and 3B.

The identifying information is organized according to the medication that it identifies. For example, images of Adderall XR (e.g., ¼ dextroamphetamine saccharate, ¼ dextroamphetamine sulfate, ¼ racemic dextro/levo-amphetamine aspartate monohydrate, and ¼ racemic dextro/levo-amphetamine sulfate) can be associated with a data identifier of Adderall XR in the item data 110.

In certain embodiments, if additional identifying information is needed, or if the item data 110 does not otherwise include certain identifying information for a medication, additional identifying information can be retrieved by the processor 104 by a request sent through the communications module 106 over the network 118 (e.g., a private communications network or public communications network, such as the Internet). Communications module 106 is configured to transmit, receive, and otherwise communicate information with network 118 and/or devices on the network 118. The system 100 can be in continuous communication with network 118, or can connect to network 118 or another device as necessary (e.g., when additional identifying information is requested). Communication is achieved via a communication layer that enables data transmissions. Example communications modules 106 include serial communication interfaces such as RS-232, Ethernet, Universal Serial Bus (USB), and wireless interfaces such as RF, infrared, Bluetooth®, and IEEE 802.11x. For example, the system 100 can be networked by connecting to a central data network device via data cables.

The verification module 112 includes instructions that are executed by the processor 104. Exemplary instructions are illustrated in the process 200 of FIG. 2, described in more detail below. In certain embodiments, the verification module 112 and item data 110 can be loaded into the memory of an automated dispensing machine, such that the illustrated system 100 is an automated dispensing machine configured with the processes disclosed herein. In certain embodiments, the verification module 112 and item data 110 can be loaded into the memory of a bedside administration system, such that the illustrated system 100 is a bedside administration system configured with the processes disclosed herein. In certain embodiments, the verification module 112 and item data 110 can be loaded into the memory of a portable device, such that the illustrated system 100 is a handheld computer (e.g., a personal digital assistant) configured with the processes disclosed herein.

The processor 104 is configured to execute instructions contained in the memory 108 of the client, such as instructions stored in the verification module 112. The processor 104 is also configured to receive input information from the input device 114 and provide identifying information from the item data 110 to the display device 116. In certain embodiments, the processor 104 is configured to process and provide identifying information for multiple items simultaneously or serially to the display device 116 for display (e.g., in a composite image). In certain embodiments where the system 100 is an automated dispensing machine including medications to be dispensed, the processor 104 is configured to dispense medication upon receipt of appropriate access information from the input device 114. In certain embodiments, the processor 104 is configured to provide, to the display device 116, information to display a physical scale for the medication, thereby providing a size reference for a medication.

The input device 114 is configured to provide input, to the client 102, the input having been processed by the processor 104. A wired or wireless input device 114 can be used, such as, but not limited to, a keyboard, a touch-screen display, a mouse, a microphone, a magnetic card reader, a biometric reader-sensor, a proximity reader, a radio frequency (RF) identification reader, and a symbology reader. In certain embodiments, the input device 114 is configured to provide, from a user, access information indicating whether the user has access to a medication. For example, the access information can include a user name, password, keycard, or other identification information known to those of skill in the art. In certain embodiments, the input device 114 is configured to receive, from a user, input indicating that the user has verified that a dispensed medication has the same identifying information as the identifying information displayed by the display module. For example, if the system 100 dispenses a vial of Heparin to a user, the system can require the user to verify the dispensed vial is marked with the same name, dose, and manufacturer as displayed by the display device 116. If the user does not verify the displayed information, such as within a predetermined amount of time, the processor 104 can output an alert, such as a visual alert (e.g., reminder to the user), audible alert, or other notification indicating the dispensed vial has not been verified. In certain embodiments, the processor 104 can also log out the current user, restrict access to (e.g., lock) the receptacle containing the item, record incomplete verification activity, and/or send a notification message to another user or system.

The display device 116 is one type of output module. Other types of output modules can be used, including, without limitation, a printer, audible indicators such as speakers, or other visual indicators such as display screens, including a cathode ray tube (CRT) display, vacuum fluorescent display (VFD), light emitting diode (LED) display, plasma display panel (PDP), liquid crystal display (LCD), organic light emitting diode (OLED), or surface-conduction electron-emitter display (SED). The display device 116 is configured to display or otherwise output information provided by the processor, such as identifying information from the item data 110 in the memory 108.

Figure 2:
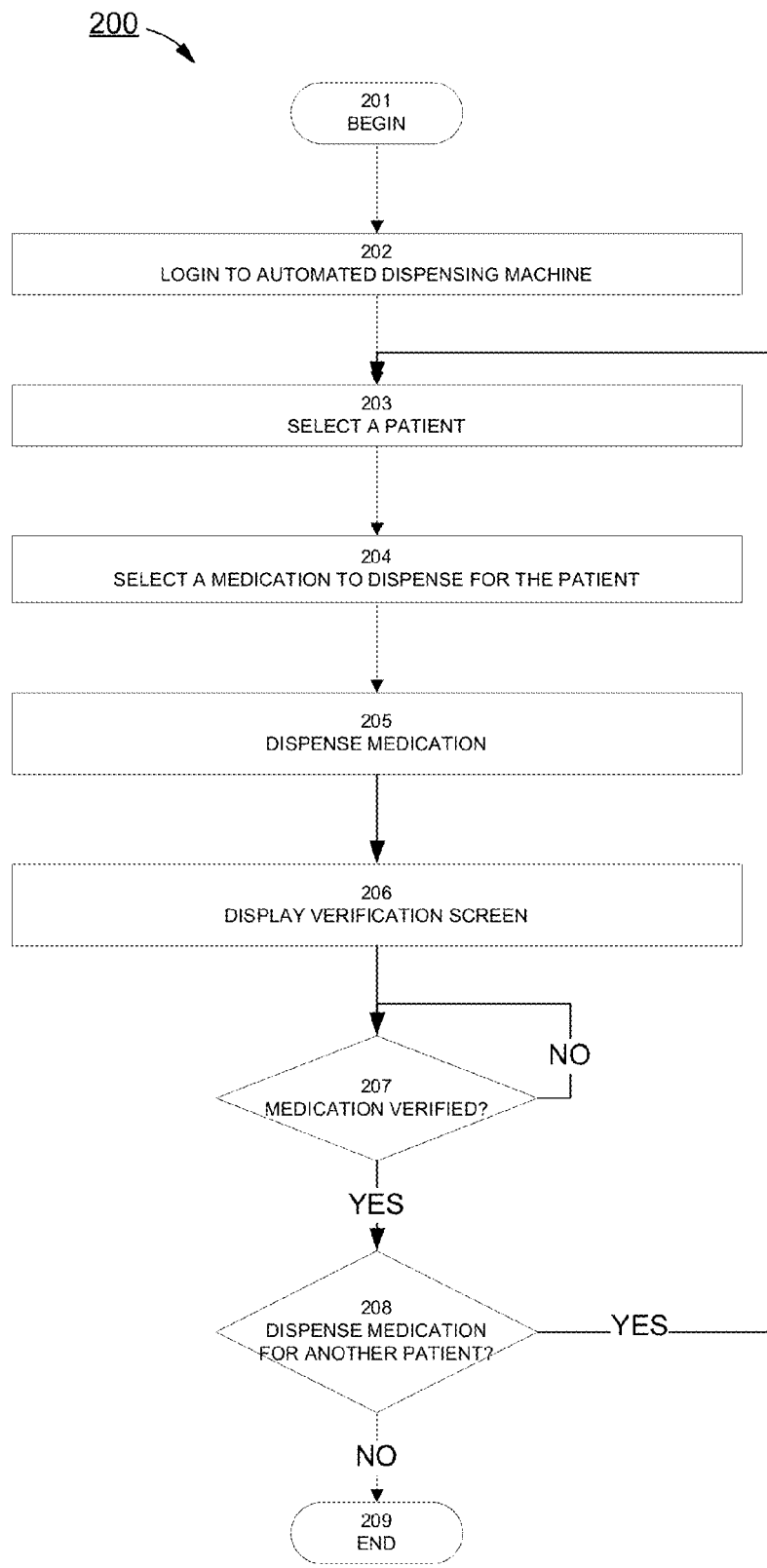
FIG. 2 is a flow chart illustrating an exemplary process of verifying the accuracy of a dispensed item using the dispensed item verification system of FIG. 1.

FIG. 2 is a flow chart illustrating an exemplary process 200 of verifying the accuracy of a dispensed item using the dispensed item verification system 100 of FIG. 1. In certain embodiments, the process 200 of FIG. 2 is embodied in verification module 112 as computer-readable instructions configured to be stored in memory (e.g., as software), which can then be loaded onto a computer system or other machine as illustrated and described in FIG. 1.

Figure 3A:
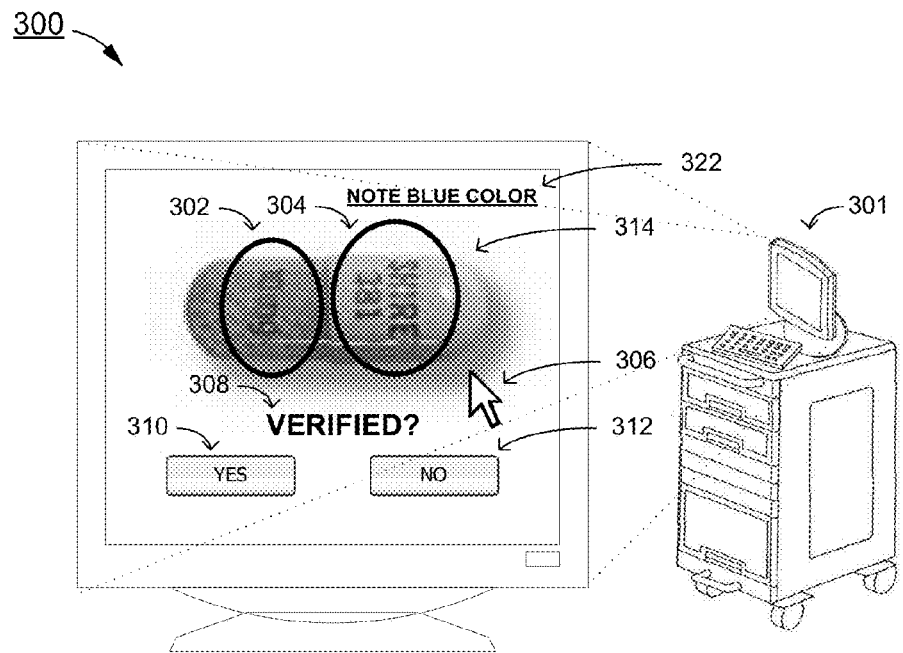
FIG. 3A is a sample screenshot displayed by the display device associated with the dispensed item verification system of FIG. 1 for verifying the accuracy of a dispensed medication pill during the operation of FIG. 2.
Figure 3B:
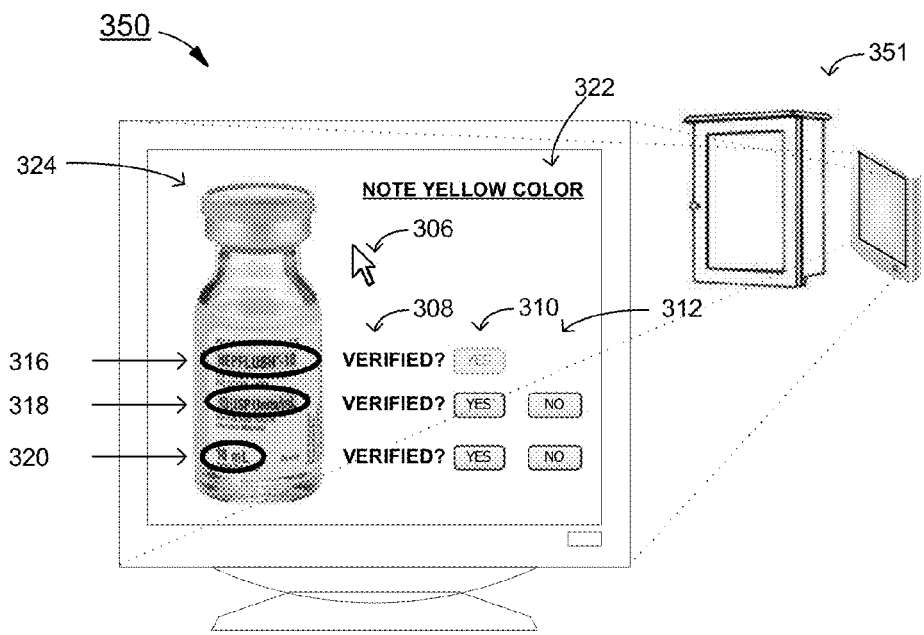
FIG. 3B is a sample screenshot displayed by the display device associated with the dispensed item verification system of FIG. 1 for verifying the accuracy of a dispensed medication bottle during the operation of FIG. 2.

The process 200 begins from step 201 to step 202 in which a user logs in to the client 102, an automated dispensing machine embodiment 301 (illustrated in FIG. 3A) of the dispensed item verification system 100, described above. The user logs in by providing authorized access information to the automated dispensing machine 301 using an input device 114. After the user logs in, the user selects a patient in step 203 for whom to dispense medication, and, in step 204, selects a medication of the patient to be dispensed. In step 205, the automated dispensing machine 301 dispenses the selected medication to the user. Next, in step 206, the automated dispensing machine 301 displays a verification screen to the user on the display device 116. Exemplary verification screens are illustrated in FIGS. 3A and 3B and will be described in detail below. The automated dispensing machine 301 then awaits user verification of the dispensed medication in decision step 207, and, when the user verifies the medication, the user is asked whether to dispense a medication for another patient in decision step 208. If the user decides to dispense a medication for another patient in decision step 208, the process 200 returns to step 203, otherwise the process 200 ends in step 209.

Having set forth in FIG. 2 a process 200 by which a dispensed item is verified using the dispensed item verification system of FIG. 1, an example will now be presented using the process 200 of FIG. 2 and the medication pill Adderall XR. The process 200 begins from step 201 to step 202 in which a nurse logs in to an automated dispensing machine 301 embodiment of the dispensed item verification system 100 by inputting his username and password using a keyboard and mouse 114. After the nurse logs in, the nurse selects to dispense medication for patient Jane Doe in step 203, and, in step 204, selects to dispense one pill of Jane Doe's prescribed Adderall XR. In step 205, the automated dispensing machine 301 dispenses one pill of Adderall XR to the nurse. Next, in step 206, the automated dispensing machine 301 displays a verification screen 300 to the nurse on the display device 116, as illustrated in FIG. 3A.

FIG. 3A is an exemplary screenshot of a verification screen 300 for the dispensing of Adderall XR. An image 314 of an Adderall XR pill is provided. Two distinct circles are provided for identifying distinguishing features of the image 314; one circle 302 identifying the 10 mg dose, and one circle 304 identifying the manufacturer, SHIRE. The nurse is also directed to identify the distinct blue coloring 322 of the pill. The nurse is prompted to verify 308 these identifying features by using a mouse pointer 306 to press buttons on the screen 300 indicating that the dispensed pill has been verified ("YES" button 310) as Adderall XR, or that that the dispensed pill has not been verified ("NO" button 312) as Adderall XR.

When the nurse verifies the medication in decision step 307 (e.g., by pressing the yes button 310 using the mouse pointer 306, the nurse is then asked whether he would like to dispense a medication for another patient in decision step 208. The nurse decides not to dispense a medication for another patient in decision step 208, and the process 200 ends in step 209.

Another example will now be presented using the process 200 of FIG. 2 and the medication vial Heparin Lock Flush Solution (i.e., HEPFLUSH-10). The process 200 begins from step 201 to step 202 in which a pharmacy technician logs in to a bedside administration system 351 embodiment of the dispensed item verification system 100 by inputting her thumbprint using a touchscreen monitor and biometric identifier (not illustrated) as input device 114. After the pharmacy technician logs in, the pharmacy technician selects to dispense medication for patient John Doe in step 203, and, in step 204, selects to dispense one vial of John Doe's prescribed Heparin Lock Flush Solution. In step 205, the bedside administration system 351 dispenses one vial of Heparin Lock Flush Solution to the pharmacy technician. Next, in step 206, the bedside administration system 351 displays a verification screen 350 to the pharmacy technician on the display device 116, as illustrated in FIG. 3B.

FIG. 3B is an exemplary screenshot of a verification screen 350 for the dispensing of a vial of Heparin Lock Flush Solution. An image 324 of a vial of Heparin Lock Flush Solution is provided. Three distinct circles are provided for identifying distinguishing features of the image 314; one circle 316 identifying the medication name, HEPFLUSH-10, one circle 318 identifying the dose, 10 USP units/mL, and one circle 320 identifying the volume, 10 mL. The pharmacy technician is also directed to identify the distinct yellow coloring 322 of the vial. The pharmacy technician is prompted to verify 308 each of these identifying features by using a mouse pointer 306 to press buttons on the screen 350 indicating that the dispensed vial has been verified 310 for each of these identifying features as Heparin Lock Flush Solution, or that that the dispensed vial has not been verified 312 for each of these identifying features as Heparin Lock Flush Solution. In this example, the pharmacy technician has already verified the medication name as illustrated by the "YES" button 310 being presented in phantom.

When the pharmacy technician verifies the medication in decision step 307 (e.g., by pressing each "YES" button 310 associated with the identifying features of the image 314 of the vial using the touch screen monitor 206, the pharmacy technician is then asked whether she would like to dispense a medication for another patient in decision step 208. The pharmacy technician decides not to dispense a medication for another patient in decision step 208, and the process 200 ends in step 209.

Figure 4:
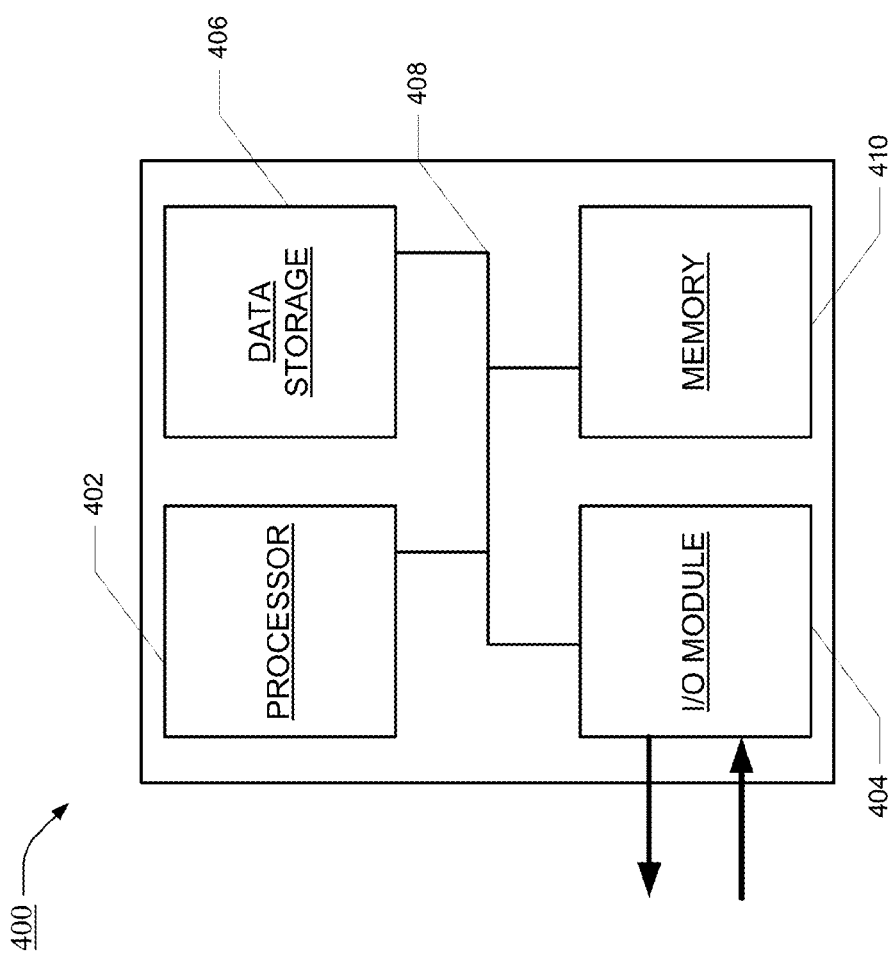
FIG. 4 is a block diagram illustrating an example of a computer system with which the dispensed item verification system of FIG. 1 can be implemented.

FIG. 4 is a block diagram illustrating an example of a computer system 400 with which the dispensed item verification system 100 of FIG. 1 can be implemented. In certain embodiments, the computer system 400 may be implemented using software, hardware, or a combination of both, either in a dedicated server, or integrated into another entity, or distributed across multiple entities.

Computer system 400 includes a bus 408 (e.g., communications bus 120 from FIG. 1) or other communication mechanism for communicating information, and a processor 402 (e.g., processor 104 from FIG. 1) coupled with bus 408 for processing information. By way of example, the computer system 400 may be implemented with one or more processors 402. Processor 402 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information. Computer system 400 also includes a memory 410 (e.g., memory 108 from FIG. 1), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 408 for storing information and instructions to be executed by processor 402. The instructions may be implemented according to any method well known to those of skill in the art, including computer languages such as system languages (e.g., C, C++, Assembly), architectural languages (e.g., Java), and application languages (e.g., PHP, Ruby, Perl, Python). Memory 410 may also be used for storing temporary variable or other intermediate information during execution of instructions to be executed by processor 402. Computer system 400 further includes a data storage device 406, such as a magnetic disk or optical disk, coupled to bus 408 for storing information and instructions.

Computer system 400 may be coupled via I/O module 404 to a display device (e.g., display device 116 from FIG. 1), such as a CRT or LCD for displaying information to a computer user. An input device (e.g., input device 114 from FIG. 1), such as, for example, a keyboard, touch screen, or a mouse may also be coupled to computer system 400 via I/O module 404 for communicating information and command selections to processor 402.

According to one aspect of the present disclosure, a system for verifying the dispensing of items can be implemented using a computer system 400 in response to processor 402 executing one or more sequences of one or more instructions contained in memory 410. Such instructions may be read into memory 410 from another machine-readable medium, such as data storage device 406. Execution of the sequences of instructions contained in main memory 410 causes processor 402 to perform the process steps described herein. One or more processors in a multi-processing arrangement may also be employed to execute the sequences of instructions contained in memory 410. In alternative embodiments, hard-wired circuitry may be used in place of or in combination with software instructions to implement various embodiments of the present disclosure. Thus, embodiments of the present disclosure are not limited to any specific combination of hardware circuitry and software.

The term "machine-readable medium" as used herein refers to any medium or media that participates in providing instructions to processor 402 for execution. Such a medium may take many forms, including, but not limited to, non-volatile media, volatile media, and transmission media. Non-volatile media include, for example, optical or magnetic disks, such as data storage device 406. Volatile media include dynamic memory, such as memory 406. Transmission media include coaxial cables, copper wire, and fiber optics, including the wires that comprise bus 408. Transmission media can also take the form of acoustic or light waves, such as those generated during radio frequency and infrared data communications. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, a carrier wave, or any other medium from which a computer can read.

The embodiments of the present disclosure provide a system in which items dispensed to users are quickly and easily verified by those users by providing a user interface in which specific identifying features of the item are presented to the user for verification. In certain embodiments, the user is required to provide feedback to the system indicating the item has been verified.

It should be appreciated from the foregoing description that while certain embodiments of the present disclosure are useful in the medical drug and supply field, other embodiments have applicability to a broad range of industries apart from the medical industry, where similar inventory verification is preferred. The present disclosure is not intended to be limited to the medical supply and drug industry.

Those of skill in the art would appreciate that the various illustrative blocks, modules, elements, components, methods, and algorithms described herein may be implemented as electronic hardware, computer software, or combinations of both. Furthermore, these may be partitioned differently than what is described. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application.

It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An automated medication dispensing system comprising:
   a memory configured to store identifying information for at least one item, the identifying information comprising an indicator associated with at least one specific feature of the at least one item;
   a processor configured to dispense the at least one item to a user;
   an output module configured to display the identifying information for the at least one item; and
   an input device configured to receive, from the user, input indicating that the user has verified that the dispensed item has the same identifying information as the identifying information displayed by the output module,
   wherein the processor is further configured to output an alert if, within a predetermined amount of time, the user has not verified that the identifying information of the dispensed item is the same as the identifying information displayed by the output module.

2. The system of claim 1, further comprising an input device configured to receive access information, wherein the processor is configured to dispense the at least one item to the user if the access information indicates the user has access to the at least one item.

3. The system of claim 1, wherein the identifying information displayed by the output module comprises an image of the at least one item.

4. The system of claim 1, wherein the at least one specific feature of the at least one item comprises at least one of a shape, color, and marking of the at least one item.

5. The system of claim 1, wherein the at least one item is a medication.

6. A handheld device comprising:
   a memory configured to store identifying information for at least one item, the identifying information comprising an indicator associated with at least one specific feature of the at least one item;
   a processor configured to receive information identifying that the at least one item has been dispensed to a user;
   a display module configured to display the identifying information for the at least one item; and
   an input device configured to receive, from the user, input indicating that the user has verified that the dispensed item has the same identifying information as the identifying information displayed by the display module,
   wherein the processor is further configured to output an alert if, within a predetermined amount of time, the user has not verified that the identifying information of the dispensed item is the same as the identifying information displayed by the output module.

7. A bedside administration system comprising:
   a cabinet housing configured to hold at least one item and configured to be accessed by an authorized user;
   a memory configured to store identifying information for the at least one item, the identifying information comprising an indicator associated with at least one specific feature of the at least one item;
   a processor configured to dispense, from the cabinet housing, the at least one item to the authorized user;
   an output module configured to display the identifying information for the at least one item; and
   an input device configured to receive, from the user, input indicating that the user has verified that the dispensed item has the same identifying information as the identifying information displayed by the output module,
   wherein the processor is further configured to output an alert if, within a predetermined amount of time, the user has not verified that the identifying information of the dispensed item is the same as the identifying information displayed by the output module.

8. A method for verifying the dispensing of an item comprising:
   receiving a selection for at least one item to be dispensed;
   dispensing the at least one item to a user;
   retrieving identifying information for the at least one item from memory, the identifying information comprising an indicator associated with at least one specific feature of the at least one item;
   displaying the identifying information for the at least one item;
   receiving, from the user, input indicating that the user has verified that the dispensed at least one item has the same identifying information as the displayed identifying information; and
   outputting an alert if, within a predetermined amount of time, the user has not verified that the identifying information of the dispensed at least one item is the same as the displayed identifying information.

9. The method of claim 8, further comprising:
   receiving access information from a user,
   wherein the at least one item is dispensed to the user if the access information indicates the user has access to the at least one item.

10. The method of claim 8, wherein the displayed identifying information comprises an image of the at least one item.

11. The method of claim 8, wherein the at least one specific feature of the at least one item comprises at least one of a shape, color, and marking of the at least one item.

12. The method of claim 8, wherein the at least one item is a medication.

13. A non-transitory computer-readable medium having computer-executable instructions for causing a processor to execute instructions to verify a dispensing of an item by performing steps comprising:
   receiving a selection for at least one item to be dispensed;
   dispensing the at least one item to a user;
   retrieving identifying information for the at least one item from memory, the identifying information comprising an indicator associated with at least one specific feature of the at least one item;
   displaying the identifying information for the at least one item; and
   receiving, from the user, input indicating that the user has verified that the identifying information of the dispensed at least one item is the same as the displayed identifying information, and
   outputting an alert if, within a predetermined amount of time, the user has not verified that the identifying information of the dispensed at least one item is the same as the displayed identifying information.

* * * * *